United States Patent
Nicholson et al.

(10) Patent No.: US 7,493,166 B2
(45) Date of Patent: Feb. 17, 2009

(54) ELECTRICAL CONTACT FOR A FEEDTHROUGH/ELECTRODE ASSEMBLY

(75) Inventors: John E. Nicholson, Blaine, MN (US); James Strom, Arden Hills, MN (US); William D. Wolf, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 11/116,965

(22) Filed: Apr. 28, 2005

(65) Prior Publication Data

US 2006/0247713 A1    Nov. 2, 2006

(51) Int. Cl.
  *A61N 1/00* (2006.01)
(52) U.S. Cl. ......................................................... 607/36
(58) Field of Classification Search ...................... 607/5, 607/9, 36, 37, 38; 429/181
  See application file for complete search history.

(56) References Cited

U.S. PATENT DOCUMENTS

| | | | |
|---|---|---|---|
| 4,476,868 A | 10/1984 | Thompson | |
| 4,940,858 A | 7/1990 | Taylor et al. | |
| 5,345,362 A | 9/1994 | Winkler | |
| 5,650,759 A | 7/1997 | Hlttman et al. | |
| 5,855,995 A | 1/1999 | Haq et al. | |
| 5,867,361 A | 2/1999 | Wolf et al. | |
| 5,870,272 A | 2/1999 | Seifried et al. | |
| 6,031,710 A | 2/2000 | Wolf et al. | |
| 6,041,496 A | 3/2000 | Haq et al. | |
| 6,055,455 A | 4/2000 | O'Phelan et al. | |
| 6,146,743 A | 11/2000 | Haq et al. | |
| 6,349,025 B1 | 2/2002 | Fraley et al. | |
| 6,512,940 B1 | 1/2003 | Brabec et al. | |
| 6,519,333 B1 | 2/2003 | Malik | |
| 6,631,290 B1 | 10/2003 | Guck et al. | |
| 6,721,602 B2 | 4/2004 | Engmark et al. | |
| 2002/0072778 A1 | 6/2002 | Guck et al. | |
| 2002/0165588 A1 | 11/2002 | Fraley et al. | |
| 2004/0258988 A1* | 12/2004 | Nielsen et al. | ............... 429/181 |
| 2005/0007718 A1 | 1/2005 | Stevenson et al. | |
| 2005/0060003 A1 | 3/2005 | Taylor et al. | |

* cited by examiner

*Primary Examiner*—George Manuel
(74) *Attorney, Agent, or Firm*—Carol F. Barry; Scott A. Bardell

(57) ABSTRACT

An implantable medical device has one or more feedthrough/electrode assemblies positioned around an outer periphery of the device. Each of the assemblies includes a ferrule and a feedthrough conductor that extends longitudinally through the ferrule. Each of the assemblies also includes a cover having an insulative body and an electrical contact that is mounted to the plastic insulator. The plastic insulator is positioned over an inner end of the assembly such that the contact is operatively coupled to the feedthrough conductor of the assembly. The cover can be oriented so as to be freely accessible for purposes of electrically connecting circuitry within the implantable medical device to the contact, and in turn, the feedthrough conductor. In turn, the wiring used in connecting the circuitry and the contact can be routed within the implantable medical device as desired.

20 Claims, 9 Drawing Sheets

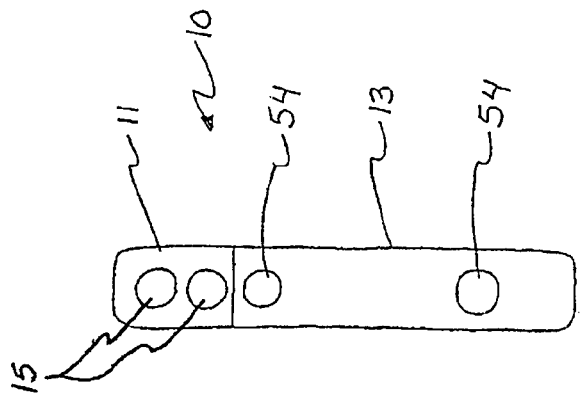
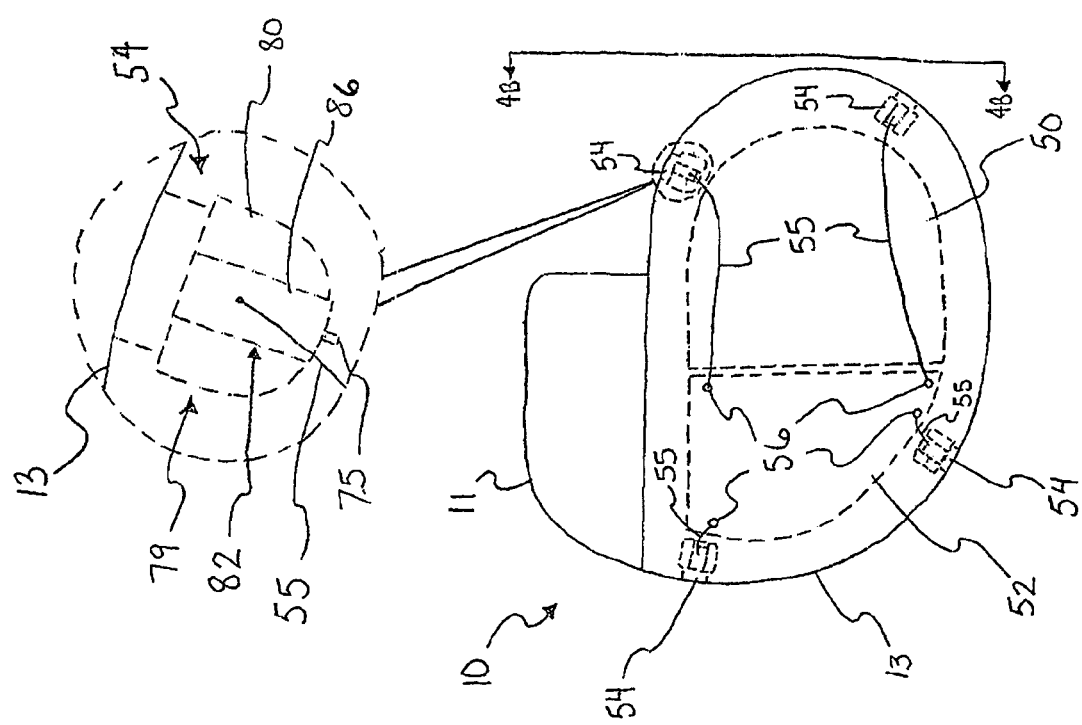
FIG. 4B
FIG. 4A

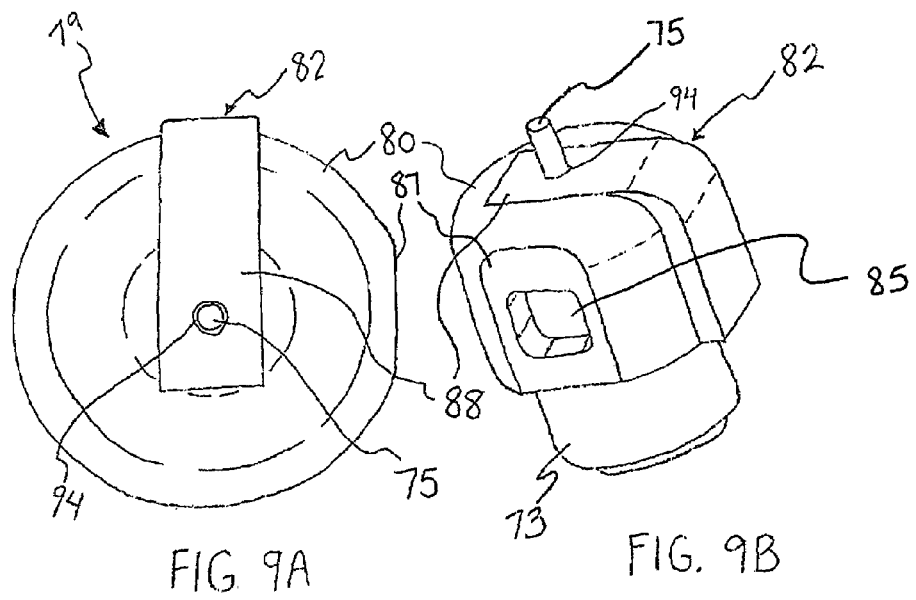
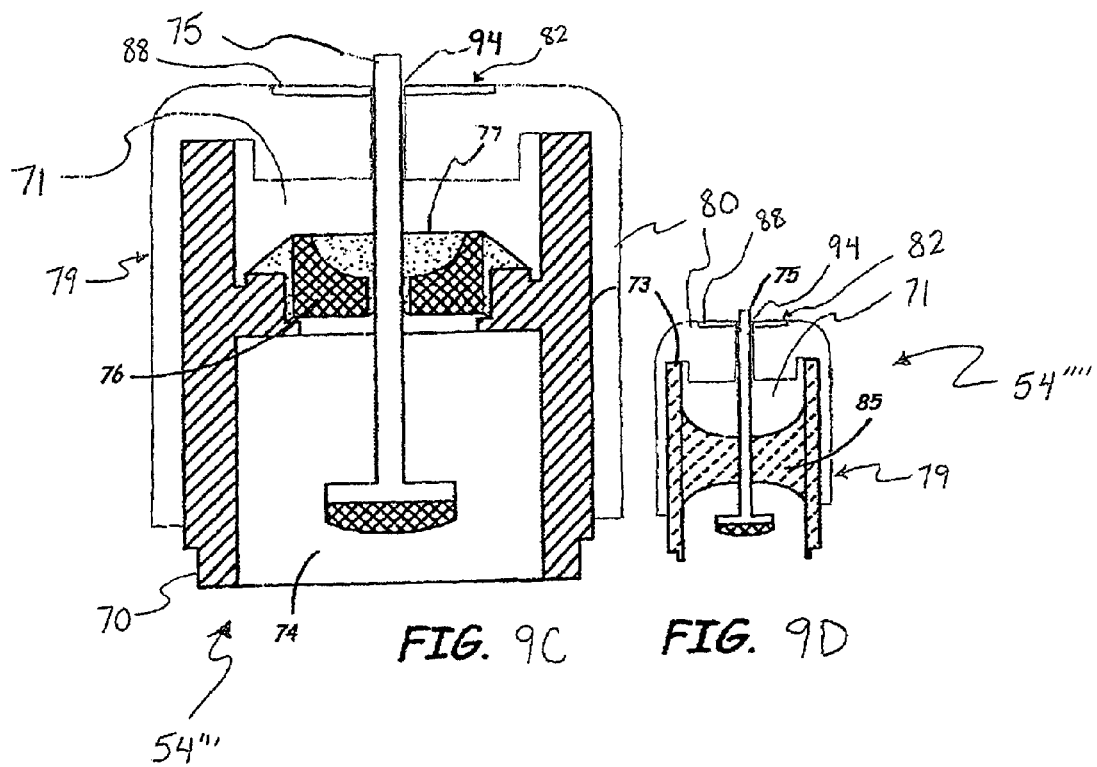

ELECTRICAL CONTACT FOR A FEEDTHROUGH/ELECTRODE ASSEMBLY

FIELD

The invention relates generally to implantable pacemakers and more particularly to subcutaneous electrodes implemented to sense, detect, and store electrocardiographic data and waveform tracings from an implanted pacemaker. More particularly, the invention relates to embodiments including the manufacture and assembly of such electrodes with feedthroughs that facilitate their electrical connection to a pacemaker's circuitry.

BACKGROUND SECTION

Electrocardiogram (ECG) signals are commonly used to determine the status of the electrical conduction system of the human heart. As practiced, an ECG recording device is commonly attached to the patient via ECG leads connected to skin electrodes arrayed on the patient's body so as to achieve a recording that displays the cardiac waveforms in any one of 12 possible vectors.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. The twelve-lead electrocardiogram is generally the first device used in determining cardiac status prior to implanting a medical device (e.g., a pacemaker) within a patient. Following implantation, the physician can typically use any of a number of ECGs to check the device's efficacy.

Prescription for implantation and programming of the medical devices are typically based on the analysis of waveforms provided using a PQRST electrocardiogram (ECG) and an electrogram (EGM). The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart.

Since the creation of the first cardiac pacemaker, implantable medical device (IMD) technology has advanced with development of further sophisticated, programmable cardiac pacemakers and pacemaker-cardioverter-defibrillator (PCD) arrhythmia control devices; such devices being designed to detect arrhythmias and dispense appropriate therapies. Detection, analysis and storage of EGM data within the implanted medical devices are well known in the art. The detection and discrimination between various arrhythmic episodes is of considerable interest in order to trigger delivery of an appropriate therapy to the patient (via the implantable medical device).

Monitoring electrical activity of the human heart for diagnostic and related medical purposes is well known in the art. For example, as mentioned, circuitry has been designed for recording ECG signals from multiple lead inputs. Similarly, other designs have employed multiple electrode systems that combine surface EKG signals for artifact rejection. The primary application of multiple electrode systems in such designs appears to be vector cardiography from ECG signals taken from multiple chest and limb electrodes. This is a technique for monitoring the direction of depolarization of the heart including the amplitude of the cardiac depolarization waves.

Numerous body surface ECG monitoring electrode systems have been implemented to detect the ECG and conduct vector cardiographic studies. For example, a four electrode orthogonal array has been applied to the patient's skin both for convenience and to ensure precise orientation of one electrode with respect to the other. Likewise, a vector cardiography system has been used for employing ECG electrodes on the patient in commonly used locations and a hex axial reference system orthogonal display has been used for displaying ECG signals of voltage versus time generated across sampled bipolar electrode pairs.

As the functional sophistication and complexity of implantable medical device systems have increased over the years, it has become necessary for such systems to include communication means between the implanted device and/or an external device, for example, a programming console, monitoring system, and similar systems. For diagnostic purposes, it is desirable that the implanted device be able to communicate information regarding the device's operational status and the patient's condition to the physician or clinician. State of the art implantable devices are available which can transmit or telemeter a digitized electrical signal to display electrical cardiac activity (e.g., an ECG, EGM, or the like) for storage and/or analysis by an external device. As such, the implanted pacemaker is designed to detect cardiac signals and transform them into a tracing that is the same as or comparable to tracings obtainable via ECG leads attached to surface (skin) electrodes.

In certain designs, a separate passive sensing reference electrode can be mounted on the pacemaker connector block or otherwise insulated from the pacemaker case. The passive electrode is implemented to provide a sensing reference electrode that is not part of the stimulation reference electrode and thus does not carry residual after-potentials at its surface following delivery of a stimulation pulse. In regard to subcutaneously implanted EGM electrodes, one or more reference sensing electrodes can be positioned (e.g., implanted) on the surface of the pacemaker case for use in monitoring ECG signals. In use, the implanted electrodes can provide an enhanced capability of detecting and gathering electrical cardiac signals via an array of relatively closely spaced subcutaneous electrodes (located on the body of an implanted device).

More recently, alternative methods and apparatus have been used for detecting electrical cardiac signals via an array of subcutaneous electrodes located on a shroud circumferentially placed on the perimeter of an implanted pacemaker. Such designs allow direct incorporation of the electrode into a feedthrough. Depending on the design, feedthrough ferrules may be welded individually into desired positions around the perimeter of an implantable pacemaker and then the feedthrough/electrodes are fabricated into the existing ferrules. Alternatively, the complete feedthrough/electrode assembly may be fabricated and then welded as one body into the pacemaker. These feedthrough/electrode assemblies are electrically connected to the circuitry of an implantable pacemaker to create a leadless Subcutaneous Electrode Array (SEA) for the purpose of detecting cardiac depolarization waveforms displayable as electrocardiographic tracings on an external device in communication with the pacemaker. When the programming head of a programmer is positioned above an implanted device equipped with a leadless SEA electrocardiographic tracing waveforms may be displayed and viewed on the programmer screen.

However, the use of such subcutaneous electrodes have revealed certain shortcomings. For example, one shortcoming involves the efficiency and effectiveness of connecting the electrodes to the internal circuitry of the pacemaker. The embodiments of the invention are directed to overcoming, or at least reducing the effects of, this and/or other shortcomings.

BRIEF SUMMARY

A feedthrough/electrode assembly of an IMD includes an electrical contact mounted in an insulative body. In certain embodiments, the contact is oriented so as to be easily accessible for electrical interconnection between the contact and circuitry within the IMD. In certain embodiments, the contact is oriented so as to be in an elevated position in order to permit direct routing of the wiring connecting the contact to circuitry within the IMD even in cases where the feedthrough/electrode assemblies and IMD circuitry are separated by other components housed within the IMD.

BRIEF DESCRIPTION OF THE DRAWINGS

FIG. 4A is a elevation view of an implanted pacemaker in accordance with the certain embodiments of the invention.

FIG. 4B is a side view of the pacemaker of FIG. 4A taken along the lines of 4B-4B of FIG. 4A.

FIGS. 9A, 9B, 9C, and 9D show four views of ECG sensing electrodes with a large surface area in accordance with the certain embodiments of the invention.

DETAILED DESCRIPTION

Figure 1:
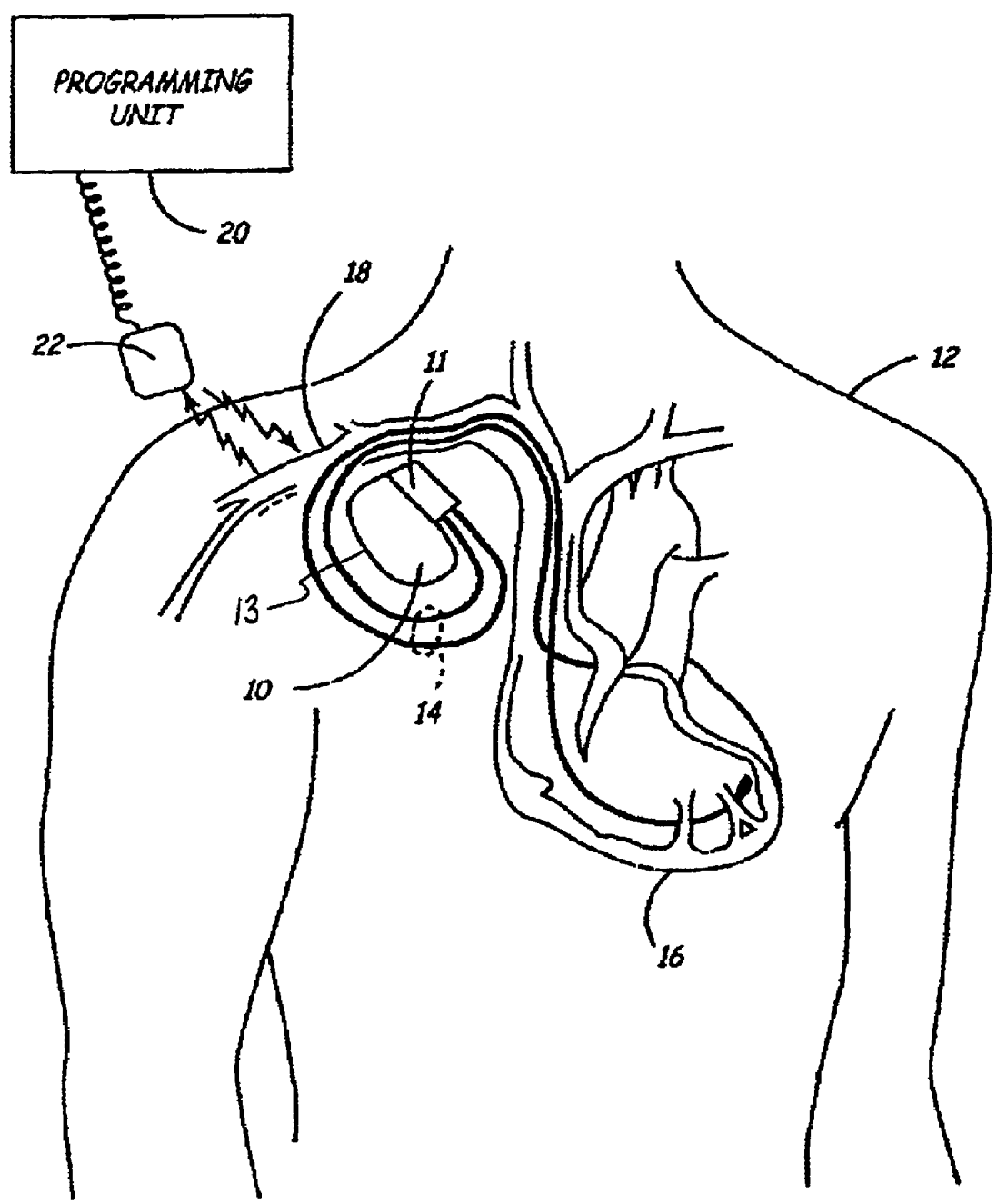
FIG. 1 is an illustration of a body-implantable device system in accordance with the certain embodiments of the invention, including a hermetically sealed device implanted in a patient and an external programming unit.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

FIG. 1 illustrates an implantable medical device system adapted for use in accordance with certain embodiments of the invention. The medical device system includes an implantable device 10 (e.g., pacemaker) in a patient 12. In accordance with conventional practice in the art, the pacemaker 10 is housed within a hermetically sealed, biologically inert outer casing 13, which may itself be conductive so as to serve as an indifferent electrode in the pacemaker's pacing/sensing circuit. One or more leads (collectively identified with reference numeral 14 in FIG. 1) of the pacemaker 10 are electrically coupled to the pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to the heart 16. As will be appreciated by those of ordinary skill in the art, the leads 14 may be implanted with their distal end(s) situated in the atrium and/or ventricle of the heart 16.

Although embodiments of the invention are described herein with references to a pacemaker, those of ordinary skill in the art having the benefit of the present disclosure will appreciate that embodiments of the invention may be practiced in connection with numerous other types of implantable medical device systems.

Also depicted in FIG. 1 is an external programming unit 20 for non-invasive communication with the pacemaker 10 via uplink and downlink communication channels, to be hereinafter described in further detail. Associated with the programming unit 20 is a programming head 22, in accordance with conventional medical device programming systems, for facilitating two-way communication between implanted device 10 and programming unit 20. In many known implantable device systems, the programming head 22 is positioned on the patient's body over the implant site of the pacemaker 10 (usually within 2- to 3-inches of skin contact), such that one or more antennae within the head 22 can send RF signals to, and receive RF signals from, an antenna disposed within the hermetic enclosure of the pacemaker 10 or disposed within a connector block 11 of the pacemaker 10, in accordance with common practice in the art.

Figure 2:
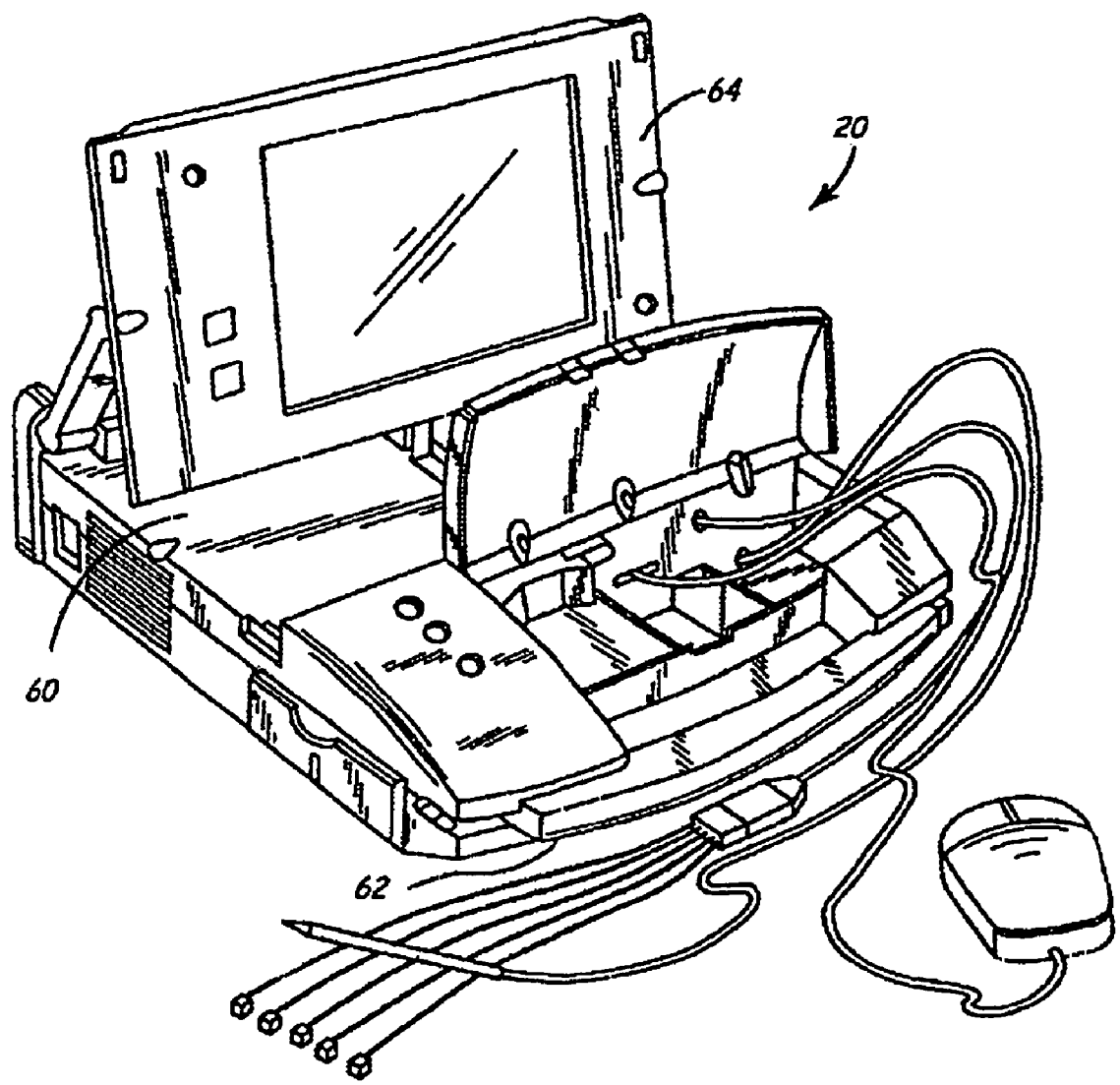
FIG. 2 is a perspective view of the external programming unit of FIG. 1.

FIG. 2 is a perspective view of the programming unit 20 in accordance with the presently disclosed embodiments of the invention.

Internally, the programming unit 20 includes a processing unit (not visibly shown) that in accordance with the embodiments of the disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, the programming unit 20 comprises an outer housing 60, which is preferably made of thermal plastic or another suitably rugged yet relatively lightweight material. A carrying handle, designated generally as 62 in FIG. 2, is integrally formed into the front of the housing 60. With the handle 62, the programming unit 20 can be carried like a briefcase. A floppy disk drive is disposed within the housing 60 and is accessible via a disk insertion slot (not shown). A hard disk drive is also disposed within the housing 60, and it is contemplated that a hard disk drive activity indicator, (e.g., an LED, not shown) could be provided to give a visible indication of hard disk activation.

An articulating display screen 64 is disposed on the upper surface of the housing 60. The display screen 64 folds down into a closed position (not shown) when the programming unit 20 is not in use, thereby reducing the size of the programming unit 20 and protecting the display surface of the display 64 during transportation and storage thereof. In the perspective view of FIG. 2, the programming unit 20 is shown with the display screen 64 having been lifted up into one of a plurality of possible open positions such that the display area thereof is visible to a user situated in front of the programming unit 20. In certain embodiments, the display screen 64 is of the LCD or electro-luminescent type, characterized by being relatively thin as compared, for example, a cathode ray tube (CRT) or the like. As would be appreciated by those of ordinary skill in the art, the display screen 64 is operatively coupled to the computer circuitry disposed within the housing 60 and is adapted to provide a visual display of graphics and/or data under control of the internal computer. The programming unit 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety; the Medtronic Model 9790 programmer is the implantable device-programming unit with which embodiments of the invention may be advantageously practiced.

In accordance with embodiments of the invention, the programming unit 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

Figure 3:
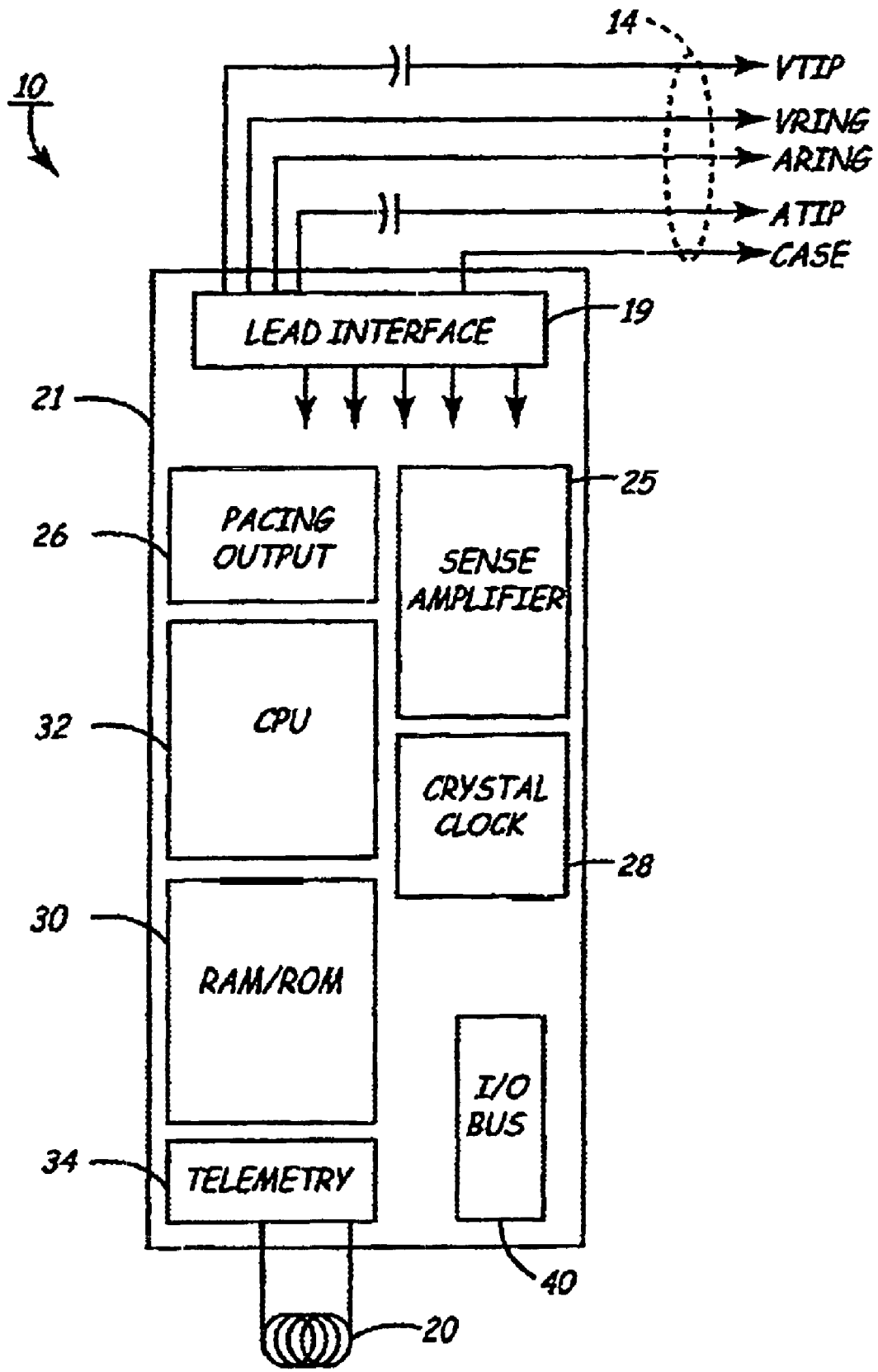
FIG. 3 is a block diagram of the implanted device from FIG. 1.

FIG. 3 is a block diagram of the electronic circuitry of the pacemaker 10 in accordance with certain embodiments of the invention. The pacemaker 10 comprises a primary stimulation control circuit 21 for controlling the device's pacing and sensing functions. The circuitry associated with the stimulation control circuit 21 may be of conventional design, in accordance, for example, with what is disclosed U.S. Pat. No. 5,052,388 issued to Sivula et al., Method And Apparatus For Implementing Activity Sensing In A Pulse Generator. To the extent that certain components of the pacemaker 10 are conventional in their design and operation, such components will not be described herein in detail, as it is believed that design and implementation of such components would be a matter of routine to those of ordinary skill in the art. For example, the stimulation control circuit 21 in FIG. 3 includes sense amplifier circuitry 25, stimulating pulse output circuitry 26, a crystal clock 28, a random-access memory and read-only memory (RAM/ROM) unit 30, and a central processing unit (CPU) 32, all of which are well-known in the art. The pacemaker 10 also includes an internal communication circuit 34 and an I/O bus 40 to aid in communicating signals with the programming unit 20.

Further referring to FIG. 3, the pacemaker 10 is coupled to one or more of the leads 14 which, when implanted, extend transvenously between the implant site of the pacemaker 10 and the patient's heart 16, as previously noted with reference to FIG. 1. Physically, the connections between the leads 14 and the various internal components of the pacemaker 10 are facilitated by means of the conventional connector block assembly 11 shown in FIG. 1. Electrically, the coupling of the conductors of the leads 14 and internal electrical components of the pacemaker 10 may be facilitated by means of a lead interface circuit 19 which functions, in a multiplexer-like manner, to selectively and dynamically establish necessary connections between various conductors in the leads 14, including, for example, atrial tip and ring electrode conductors ATIP and ARING and ventricular tip and ring electrode conductors VTIP and VRING, and individual electrical components of the pacemaker 10, as would be familiar to those of ordinary skill in the art. For the sake of clarity, the specific connections between the leads 14 and the various components of the pacemaker 10 are not shown in FIG. 3, although it will be clear to those of ordinary skill in the art that, for example, the leads 14 will necessarily be coupled, either directly or indirectly, to the sense amplifier circuitry 25 and the stimulating pulse output circuit 26, in accordance with common practice, such that cardiac electrical signals may be conveyed to the sensing circuitry 25, and such that stimulating pulses may be delivered to cardiac tissue, via the leads 14. Also not shown in FIG. 3 is the protection circuitry commonly included in implanted devices to protect, for example, the sensing circuitry of the device from high voltage stimulating pulses.

As previously noted, the stimulation control circuit 21 includes a central processing unit 32 which may be an off-the-shelf programmable microprocessor or micro controller, but in embodiments of the invention is a custom integrated circuit. Although specific connections between the CPU 32 and other components of the stimulation control circuit 21 are not shown in FIG. 3, it will be apparent to those of ordinary skill in the art that the CPU 32 functions to control the timed operation of the stimulating pulse output circuit 26 and the sense amplifier circuit 25 under control of programming stored in RAM/ROM unit 30. It is believed that those of ordinary skill in the art will be familiar with such an operative arrangement.

With continued reference to FIG. 3, the crystal oscillator circuit 28, in certain embodiments, is a 32,768-Hz crystal controlled oscillator provides main timing clock signals to the stimulation control circuit 21. Again, the lines over which such clocking signals are provided to the various timed components of pacemaker 10 (e.g., microprocessor 32) are omitted from FIG. 3 for the sake of clarity.

It is to be understood that the various components of pacemaker 10 depicted in FIG. 3 are powered by means of a battery (not shown) that is contained within the hermetic enclosure of pacemaker 10, in accordance with common practice in the art. For the sake of clarity, the battery and the connections between it and the other components of pacemaker 10 are not shown.

The stimulating pulse output circuit 26, which functions to generate cardiac stimuli under control of signals issued by the CPU 32, may be, for example, of the type disclosed in U.S. Pat. No. 4,476,868 to Thompson, entitled Body Stimulator Output Circuit, which patent is hereby incorporated by reference herein in its entirety. Again, however, it is believed that those of ordinary skill in the art could select from among many various types of prior art pacing output circuits that would be suitable for the purposes of practicing the invention.

The sense amplifier circuit 25, which is of conventional design, functions to receive electrical cardiac signals from the leads 14 and to process such signals to derive event signals reflecting the occurrence of specific cardiac electrical events, including atrial contractions (P-waves) and ventricular contractions (R-waves). CPU provides these event-indicating signals to the CPU 32 for use in controlling the synchronous stimulating operations of pacemaker 10 in accordance with common practice in the art. Additionally, in using the I/O bus 40 and internal communication circuit 34, these event-indicating signals may be communicated via uplink transmission to the external programming unit 20 for visual display to a physician or clinician.

Those of ordinary skill in the art will appreciate that the pacemaker 10 may include numerous other components and subsystems, for example, activity sensors and associated circuitry. The presence or absence of such additional components in the pacemaker 10, however, is not believed to be pertinent to embodiments of the invention, which relates primarily to the implementation and operation of communication subsystem 34 in the pacemaker 10, and an associated communication subsystem in the external unit 20.

FIGS. 4A and 4B respectively illustrate an elevation view and a cross sectional view of the pacemaker 10 in which the embodiments of the invention are implemented. The pacemaker 10 includes a hermetic casing 13 and houses electronic circuitry 52 and a hermetic power source 50. The lead connector module 11 provides an enclosure in which the proximal ends of atrial and ventricular leads may be inserted into openings 15. The lead connector module 11 is connected to the casing 13 of the pacemaker 10 and, as is well known in the art, includes electrical connections (not shown) between lead connectors and hermetic feedthroughs (also not shown).

Further referring to FIG. 4A, feedthrough/electrode assemblies 54 are welded into place on a generally or substantially flattened periphery (shield edges) of the pacemaker casing 13. While the assemblies are referenced as 54 in FIG. 4A, embodiments of the invention are further described herein by which the assemblies 54 are correspondingly referenced as 54', 54", 54''', and 54''''. In certain embodiments, the complete periphery of the pacemaker 10 may be manufactured with a slightly flattened perspective including rounded edges to accommodate the placement of the feedthrough/electrode assemblies 54 such as those disclosed in the embodiments of the invention. The assemblies 54, in certain embodiments, are welded to the casing 13 of the pacemaker 10 for integral hermiticity, and are electrically connected to the electronic circuitry 52 of the pacemaker 10 via wiring 55 routed to separate feedthroughs 56. It is to be further understood that the invention is not limited to any particular current level (high, medium, or low) of battery.

Figure 5A:
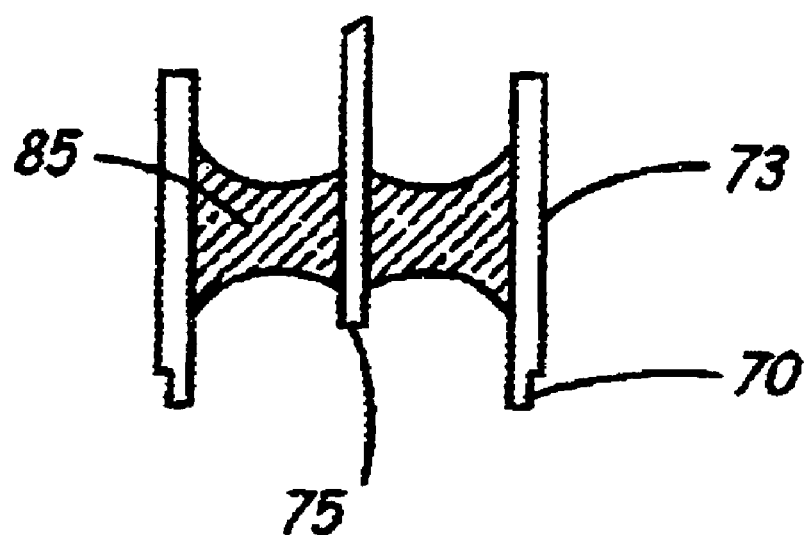
FIGS. 5A and 5B provide cross sectional views of alternative fabrications of partial assemblies of simple ECG sensing electrodes in accordance with the certain embodiments of the invention.
Figure 5B:
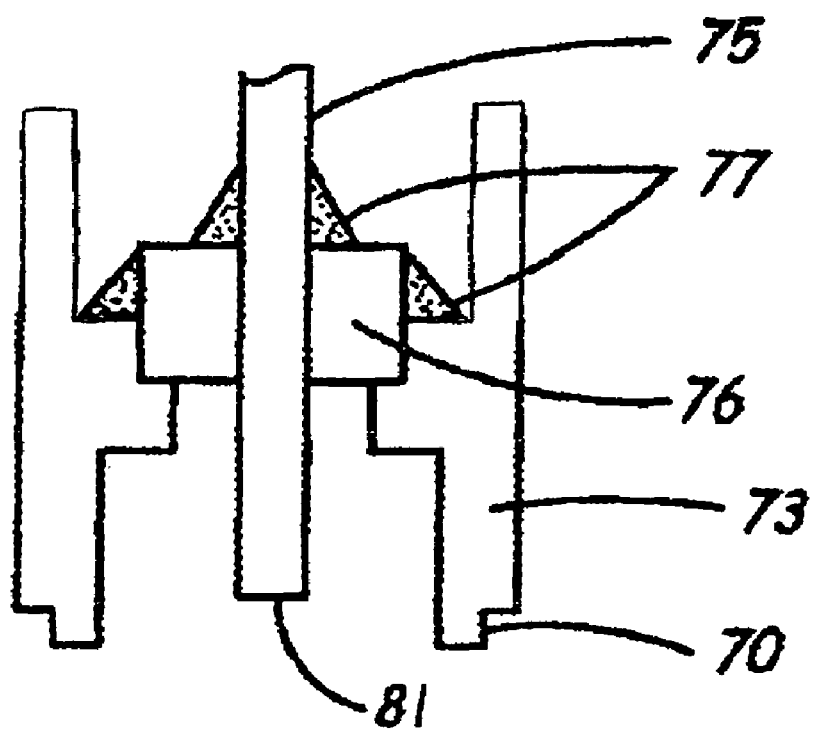

The partial assemblies of subcutaneous ECG electrode assemblies, shown in FIGS. 5A and 5B (and in FIGS. 7A and 7B), in FIGS. 8A through 8D (and in FIGS. 9A through 9D), and otherwise described or referenced herein, have feedthroughs 75. As is known, the feedthroughs are used as sensors for ECGs or EKGs and are designed to be welded into the shields of the implantable medical devices. In certain embodiments, the feedthroughs 75 have a conductive or low impedance material applied at one end, generally known as the feedthrough terminal pin (and generally extending outward toward the periphery of the implantable medical device). The electrode, or conductive material, can be a wide variety of materials. The feedthrough terminal pin can be formed to take the shape of a nailhead, or conversely, can just involve an unshaped end of the feedthrough so as to reduce the general size of the feedthrough. In certain embodiments, the feedthrough terminal pin and ferrule of the partial assembly are hermetically sealed to an insulator material by brazing or glassing.

FIGS. 5A and 5B respectively illustrate partial assemblies of simple subcutaneous ECG electrode assemblies 54' and 54" (respectively shown in FIGS. 7A and 7B) in accordance with certain embodiments of the invention. The embodiments shown in FIGS. 5A and 5B disclose assemblies having a low profile. Further, the assemblies have no appreciable protrusions and as such, lend themselves to an easier implant procedure and greater comfort for the patient.

FIG. 5A shows a feedthrough conductor 75, mounted in ferrule 73 with optional welding notch 70 to accommodate the welding of the pacemaker casing (not shown) to ferrule 73. Glass insulator 85 joins feedthrough conductor 75 and ferrule 73. In certain embodiments, feedthrough conductor 75 is machined to function as an ECG sensing electrode. P-8787, Thin Film Electrodes for Sensing Cardiac Depolarization Signals, by Guck et al, filed on Dec. 13, 2000, Ser. No. 09/736,046, disclosed a manufacturing process for conversion of feedthrough conductors to ECG electrodes. FIG. 5B displays a brazed feedthrough 81 with the conductor 75 that is supported by insulator 76 and ferrule 73. In certain embodiments, these components are joined with gold braze 77.

Figure 6:
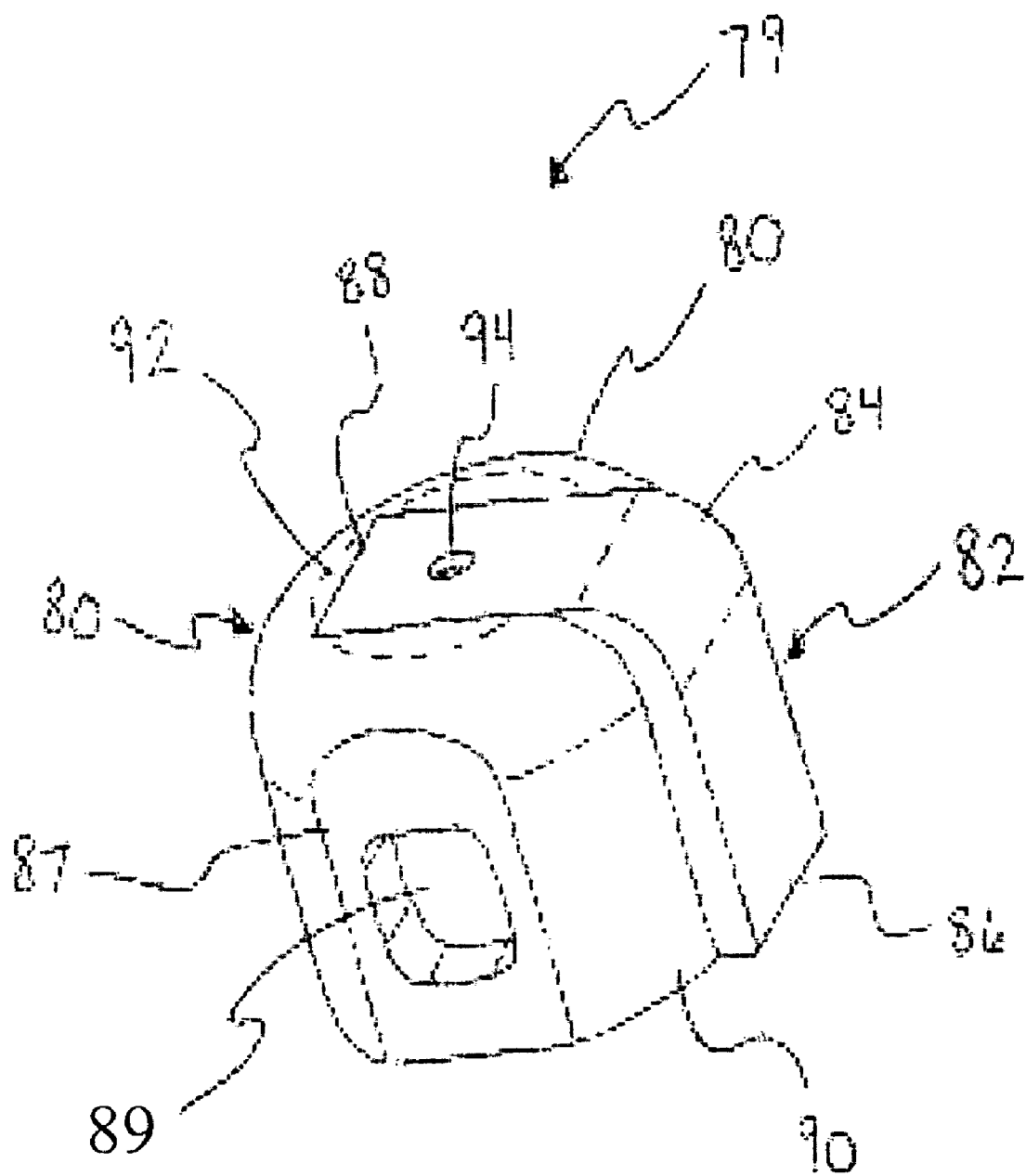
FIG. 6 provides a partial assembly of sensing electrodes in accordance with the certain embodiments of the invention.

In certain embodiments, the electrode assemblies 54', 54" (respectively shown in FIGS. 7A and 7B) include another partial assembly, namely a cover 79, as shown in FIG. 6. The cover 79 has a insulative body 80 and an electrical contact 82 that is mounted to the body 80. In certain embodiments, the insulative body 80 is plastic, however, the body 80 can be formed of other suitable non-conductive materials as well. The contact 82 is a metallic plate. In certain embodiments, the contact 82 is nickel, however, the contact 82 could be formed of other suitable materials including titanium, niobium, kovar or MP35N alloys. In certain embodiments, some of the materials, e.g., nickel or kovar, could be gold plated to aid in the coupling (e.g., welding) of the contact 82. The contact 82 has a bend 84 along its length so as to define a first contact portion 86 and a second contact portion 88, where the bend 84 lies between both portions 86, 88. In certain embodiments, the portions 86, 88 are oriented about 90 degrees from each other. One of the contact portions 86 is mounted to an outer side 90 of the insulative body 80, while the other contact portion 88 is positioned so as to extend across the top end 92 of the body 80. In certain embodiments, the cover 79 additionally includes one or more apertures 89 defined by the outer side 90 of the insulative body 80. Such apertures 89 are designed to retain adhesive (not shown) generally used to secure the cover 79 to an outer surface of the ferrule 73. In certain embodiments, the apertures 89 are defined within flat portions 87 of the cover 79, where such flat portions 87 can be used when orienting the cover 79 during its assembly to the ferrule 73 of the electrode assembly.

Figure 7A:
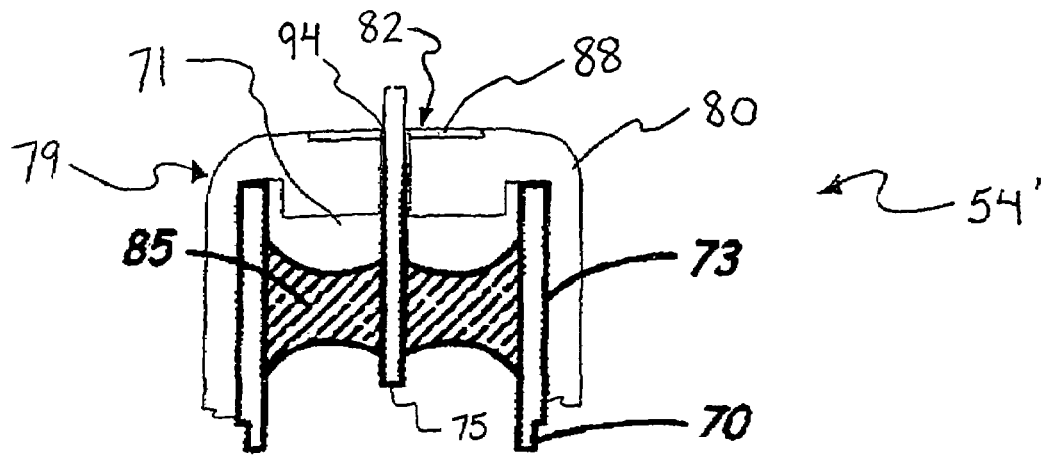
FIGS. 7A and 7B provide cross sectional views of alternative fabrications of simple ECG sensing electrodes in accordance with the certain embodiments of the invention.
Figure 7B:
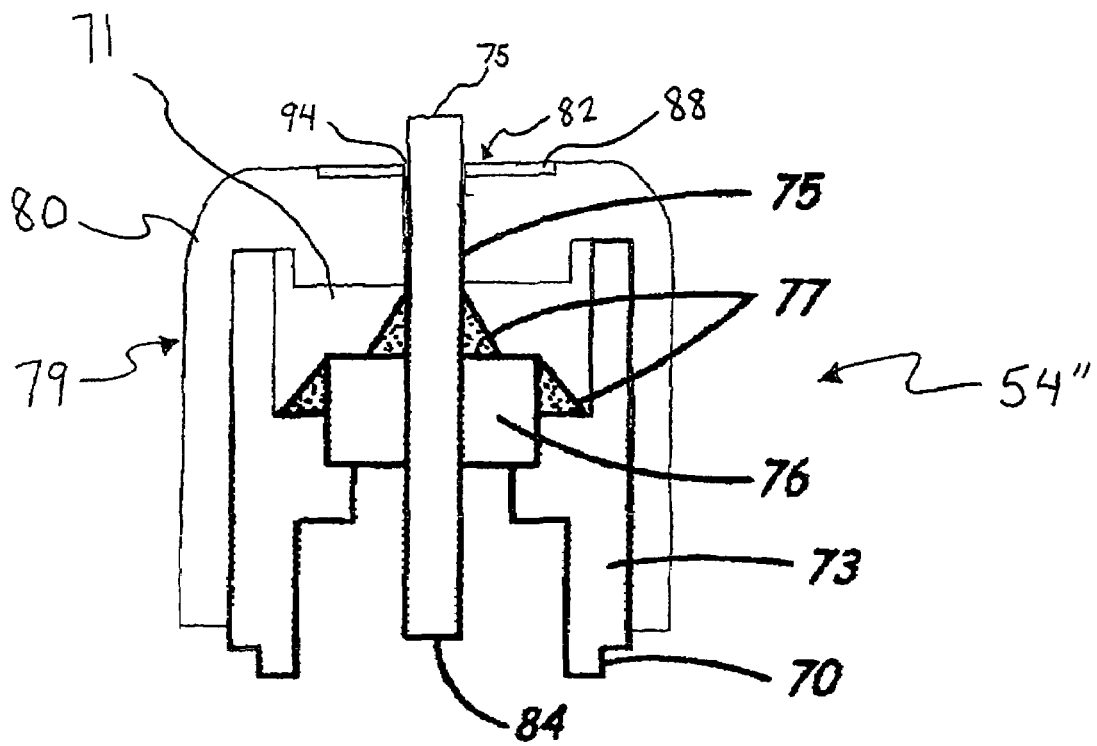

As shown in FIGS. 7A and 7B with respect to each of the electrode assemblies 54' and 54", the cover 79 is positioned over an inner end 71 of the ferrule 73 such that the contact 82 joins with the feedthrough conductor 75. In certain embodiments, the contact portion 88 joined with the feedthrough conductor 75 includes a bore 94 through which the feedthrough conductor 75 extends. The feedthrough conductor 75 and such contact portion 88 are operatively coupled, e.g., by a welding process, so as to electrically connect the feedthrough conductor 75 and the contact 82.

In certain embodiments, with reference to FIG. 4A, the pacemaker 10 is provided, wherein the electrode assemblies 54 can include one of the electrode assemblies 54', 54" as respectively shown in FIGS. 7A and 7B. As shown in the inset of FIG. 4A, the contact portion 86 mounted to the insulative body 80, in certain embodiments, is oriented (by rotating the electrode assembly) so that it is vertically accessible. As such, accessibility to the contact portion 86 in increased for purposes of electrically connecting the circuitry 52 within the pacemaker 10 to the contact body 82 (and in turn, the feedthrough conductor 75). The wire 55 is used to electrically connect the circuitry 52 within the pacemaker 10 to the contact portion 86 of the feedthrough/electrode assemblies 54', 54'''. In certain embodiments, the wire 55 is welded to the contact portion 86. With such connection to the contact portion 86, the wire is generally elevated in relation to the feedthrough conductor 75. As a result, the wire 55 can be directly routed from the circuitry 52 to the contact portion 86 (e.g., over other components in the pacemaker 10) with a reduced risk of damaging the wire 55. In certain embodiments, the wire 55 is a laser ribbon. As should be appreciated, the connection and any subsequent routing of the wire 55 is made easier in using the embodiments of the invention.

Figure 8A:
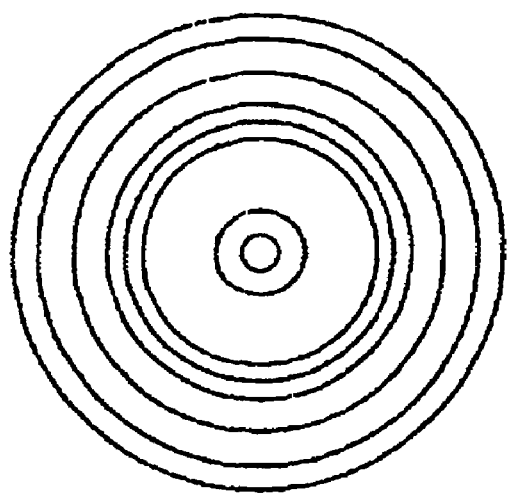
FIGS. 8A, 8B, 8C, and 8D show four views of partial assemblies of ECG sensing electrodes with a large surface area in accordance with the certain embodiments of the invention.
Figure 8B:
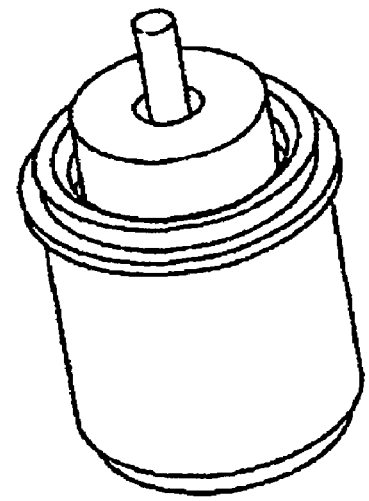
Figure 8C:
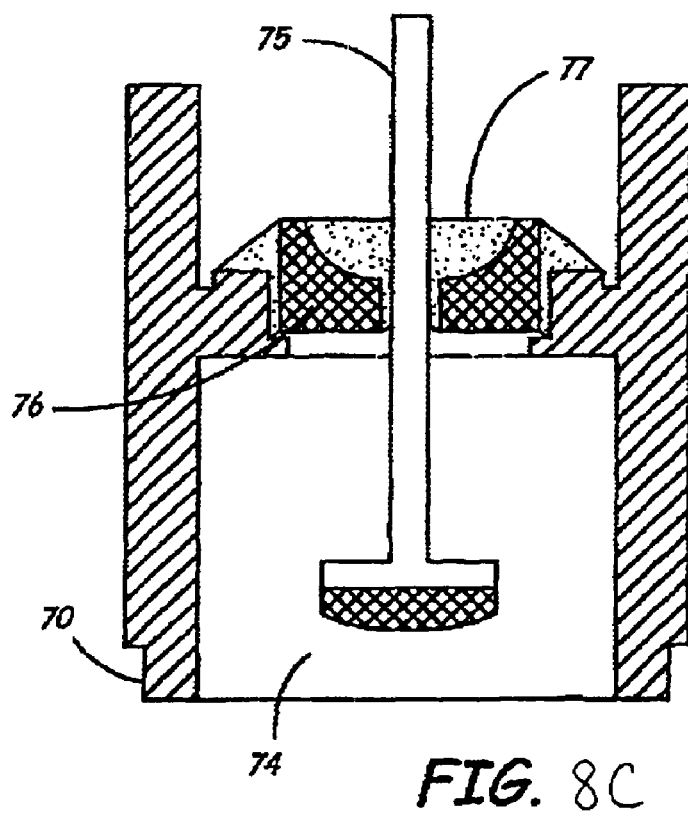
Figure 8D:
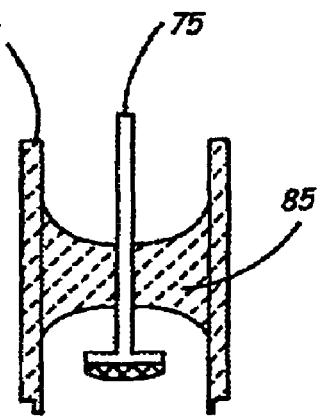

FIGS. 8A through 8D show different views of a partial assembly of an ECG sensing electrode 54''' or 54'''' (both of which are represented in FIGS. 9A through 9D) in accordance with certain embodiments of the invention. FIG. 8A is a top view and FIG. 8B is a perspective view. FIGS. 8C and 8D respectively illustrate alternate constructions of the partial assembly in cross section.

Referring to FIG. 8C, the feedthrough conductor 75 terminates in a substantially flat-ended electrode 74. In certain embodiments, the electrode 74 is recessed within ferrule 73 that is welded to the pacemaker casing at optional welding notch 70. Thus, the complete assembly has no components that protrude above or outside of the pacemaker's casing. However, the invention should not be limited as such. In other embodiments, the electrode 74 can alternatively be flush mounted or even protrude from the pacemaker's casing for better wetting of the electrode 74 during its use. The feedthrough conductor 75 extends through an opening in an insulator 76 to which it is joined by braze 77. The insulator 76 maintains electrical isolation of the ECG signal as it circuits from the sensing electrode 74 through the feedthrough conductor 75 that is electrically connected to the circuitry 52 within the pacemaker 10 (see FIG. 4A). Braze 77 serves to hermetically seal the assembly and prevent the intrusion of body fluid that fills the cavity around the electrode 74.

As shown, the geometric surface area of the ECG sensing electrode 74 is increased to improve detection of cardiac waveforms that have lesser amplitudes, for example, atrial fibrillation waves. In addition, increasing the geometric surface area may attenuate polarization effects at or around the ECG sensing electrode 74. Both features help to ensure the appropriate detection of ECG waveforms. The structure enables adequate detection, and transmission of cardiac depolarization signals. In an alternate embodiment, electrode coatings may be used to obtain larger surface areas and effect low polarization. Coating deposition methods may include sintering (powder metallurgy), sputtering, plating, CVD, PVD, or other methods. In addition, ion etching, directional solidification, or other processes may be used to texture the surface to increase the surface area of the electrode and to simplify manufacturability. Depending on the dimensions of an electrode a variety of coating materials can be applied to improve performance (e.g., reduce impedance of the structure). For example ruthenium oxide (RuO) and titanium nitride (TiN) improve performance of the relatively smaller electrodes and platinum black (PtC) has been shown to adequately improve performance of relatively larger electrodes.

FIG. 8D shows a cross sectional view of the same embodiment in which the same feedthrough conductor 75 and sensing electrode 74 are used, with the exception that glass 85 is used to i) join the feedthrough conductor 75 and electrode 74 with the ferrule 73, ii) electrically insulate so as to maintain signal integrity, and iii) hermetically seal the assembly.

In certain embodiments, the electrode assemblies 54''', 54'''' (both shown in FIG. 9) include another partial assembly, namely the cover 79 shown in FIG. 6. As illustrated in FIGS. 9A and 9B with respect to each of the electrode assemblies 54''' and 54'''', the cover 79 is positioned over an inner end 71 of the ferrule 73 such that the contact 82 joins with the feedthrough conductor 75. In certain embodiments, the contact portion 88 joined with the feedthrough conductor 75 includes a bore 94 through which the feedthrough conductor 75 extends. The feedthrough conductor 75 and such contact portion 88 are operatively coupled, e.g., by a welding process, so as to electrically connect the bodies feedthrough conductor 75 and the contact 82.

In certain embodiments, with reference to FIG. 4A, the pacemaker 10 is provided, wherein the electrode assemblies 54 can include one of the electrode assemblies 54''', 54'''' as respectively shown in FIGS. 9C and 9D. The contact portion 86 mounted to the insulative body 80 (shown in the inset of FIG. 4A), in certain embodiments, is oriented (by rotating the electrode assembly) so that it is vertically accessible. As such, accessibility to the contact portion 86 in increased for purposes of electrically connecting the circuitry 52 within the pacemaker 10 to the contact body 82 (and in turn, the feedthrough conductor 75). The wire 55 is used to electrically connect the circuitry 52 within the pacemaker 10 to the contact portion 86 of the feedthrough/electrode assemblies 54''', 54''''. In certain embodiments, the wire 55 is welded to the contact portion 86. With such connection to the contact portion 86, the wire is generally elevated in relation to the feedthrough conductor 75. As a result, the wire 55 can be directly routed from the circuitry 52 to the contact portion 86 (e.g., over other components in the pacemaker 10) without a reduced risk of damaging the wire 55. In certain embodiments, the wire 55 is a laser ribbon. As should be appreciated, the connection and any subsequent routing of the wire 55 is made easier in using embodiments of the invention.

Other variations of feedthrough conductors and sensing electrodes can be utilized, examples of which are further illustrated in Subcutaneous Sensing Feedthrough/Electrode Assembly, by Fraley et al., filed on May 7, 2001, Ser. No. 09/850,331, which are specifically incorporated by reference herein. As should be appreciated, such variations can be further utilized with the cover 79 illustrated in FIG. 6 so as to further aid in efficiently and effectively connecting the electrodes to the internal circuitry 52 of the pacemaker 10, as depicted in FIG. 4. In addition, by using such cover 79, ribbon wiring or the like can be used in coupling the contact 82 to the internal circuitry 10, and as such, the wiring can be routed as desired.

It will be appreciated the embodiments of the invention can take many forms. The true essence and spirit of the embodiments of the invention are defined in the appended claims, and it is not intended the embodiments of the invention presented herein should limit the scope thereof.

The invention claimed is:

1. A feedthrough/electrode assembly at least partially housed in an IMD comprising:
   a ferrule having a longitudinal axis and an outer longitudinal surface;
   an electrode disposed within the ferrule;
   a relatively low impedance material disposed over at least a portion of said electrode
   an insulator disposed between the electrode and the ferrule;
   a conductor extending from the electrode, the conductor extending longitudinally through the ferrule and protruding from the ferrule at one end; and
   a cover located over the ferrule at the one end and extending along the ferrule outer longitudinal surface, the cover comprising an insulative body and an electrical contact mounted directly to an outer surface of the insulative body, the electrical contact electrically coupled with the conductor at the one end and having a portion extending over the insulative body along the ferrule longitudinal outer surface accessible for electrical connection to the IMD.

2. The assembly of claim 1, wherein the IMD comprises a pacemaker.

3. The assembly of claim 1, wherein the feedthrough/electrode assembly comprises an ECG sensing electrode.

4. The assembly of claim 1, wherein a plurality of the feedthrough/electrode assemblies are distributed around an exposed periphery of the IMD forming an array.

5. The assembly of claim 1, wherein the insulator comprises a glass material.

6. The assembly of claim 1, wherein the contact comprises a plate.

7. The assembly of claim 1, wherein the contact comprises a nickel material.

8. The assembly of claim 1, wherein the contact is coupled to one or more outer surfaces of the insulative body.

9. The assembly of claim 1, wherein the contact extends longitudinally across the outer surface of the insulative body.

10. The assembly of claim 1, wherein the contact includes a bend along its length so as to define first and second portions of the contact, wherein the bend is located between the first and second portions of the contact.

11. The assembly of claim 10, wherein the first and second portions of the contact are oriented about 90 degrees apart.

12. The assembly of claim 10, wherein the first contact portion is operatively coupled to the conductor and the second contact portion is accessible from the outer longitudinal surface of the insulative body.

13. The assembly of claim 1, wherein the portion of the contact accessible from the outer longitudinal surface of the insulative body is operatively coupled to wiring, wherein the wiring electrically connects the contact portion to a circuit of the IMD.

14. A method of increasing accessibility to an electrical contact of a feedthrough/electrode assembly at least partially housed in an IMD, comprising:
    providing an IMD with a ferrule having a longitudinal axis and having an electrode disposed within the ferrule, an insulator disposed between the electrode and the ferrule, and a conductor extending from the electrode, the conductor extending longitudinally through the ferrule and protruding from the ferrule;
    disposing a cover over the ferrule at the one end, the cover comprising an insulative body and a contact mounted directly to an outer surface of the insulative body, a portion of the contact accessible from an outer longitudinal surface of the insulative body;
    operatively coupling the contact with the conductor at the one end; and
    a relatively low impedance material coupled to at least a portion of the surface of the electrode.

15. The method of claim 14, wherein the step of disposing a cover further includes rotating the cover so that the contact portion accessible from the outer longitudinal surface of the insulative body is vertically accessible for coupling thereto.

16. The method of claim 14, wherein the step of operatively coupling the contact comprises welding the contact with the conductor at the one end.

17. The method of claim 15, further comprising the step of electrically connecting the contact portion to a circuit within the IMD via wiring, wherein the wiring is directly routed from the contact portion to the circuit even when the feedthrough/electrode assembly and the circuit are separated by other components housed within the IMD.

18. A feedthrough/electrode assembly at least partially housed in an IMD comprising:
    a ferrule having a longitudinal axis;
    an electrode disposed within the ferrule;
    an insulator disposed between the electrode and the ferrule;
    a conductor extending from the electrode, the conductor extending longitudinally through the ferrule and protruding from the ferrule at one end;
    a contact operatively coupled with the conductor at the one end and having a bore through which the conductor extends therethrough at the one end, the contact extending longitudinally across an outer longitudinal surface of the ferrule; and
    a relatively low impedance material disposed over at least a portion of the surface of said electrode.

19. The assembly of claim 18, further comprising an insulative body located between the contact and the ferrule.

20. A feedthrough/electrode assembly at least partially housed in an IMD comprising:
    a ferrule having a longitudinal axis and an outer longitudinal surface;
    an electrode disposed within the ferrule;
    a relatively low impedance material disposed over at least a portion of said electrode
    an insulator disposed between the electrode and the ferrule;
    a conductor extending from the electrode, the conductor extending longitudinally through the ferrule and protruding from the ferrule at one end; and
    a cover located over the ferrule at the one end, the cover comprising
        an insulative body comprising a longitudinal outer surface extending over the ferrule outer longitudinal surface and an aperture defined by the body longitudinal outer surface for receiving an adhesive for coupling to the ferrule, and
        an electrical contact mounted directly to an outer surface of the insulative body, the electrical contact comprising a first portion, a second portion, and an approximately ninety degree bend separating the first portion and the second portion,
        the first portion extending over the body at the one end and electrically coupled with the conductor at the one end,
        the second portion extending along the body longitudinal outer surface and being accessible for electrical connection to the IMD.

* * * * *